United States Patent
Ooms et al.

[11] Patent Number: 5,593,944
[45] Date of Patent: Jan. 14, 1997

[54] AMINOARYL-1,3-OXAZINE-2,4-DIONES

[75] Inventors: Pieter Ooms, Krefeld; Hans-Joachim Santel; Markus Dollinger, both of Leverkusen, all of Germany

[73] Assignee: Bayer Aktiengesellschaft, Leverkusen, Germany

[21] Appl. No.: 284,763

[22] Filed: Aug. 2, 1994

[30] Foreign Application Priority Data

Aug. 9, 1993 [DE] Germany ............... 43 26 649.5

[51] Int. Cl.$^6$ .............. A01N 43/86; C07D 265/12; C07D 265/10
[52] U.S. Cl. .............. 504/240; 504/243; 544/92; 544/93; 544/97
[58] Field of Search .............. 544/92, 93, 97; 504/240, 243

[56] References Cited

U.S. PATENT DOCUMENTS

| | | | |
|---|---|---|---|
| 3,920,653 | 11/1975 | Wenzelburger et al. | 260/256.4 |
| 5,164,498 | 11/1992 | Ooms et al. | 544/94 |

FOREIGN PATENT DOCUMENTS

| | | |
|---|---|---|
| 0371240 | 6/1990 | European Pat. Off. |
| 0529402 | 3/1993 | European Pat. Off. |
| 2260859 | 6/1974 | Germany. |

OTHER PUBLICATIONS

Ozaki et al., Heterocycles, (1988), 27(9), 2063–2066.
Ozaki et al, Chemical Abstracts, 1971, vol. 74, entry No. 74:53811.

*Primary Examiner*—Matthew V. Grumbling
*Attorney, Agent, or Firm*—Sprung Horn Kramer & Woods

[57] ABSTRACT

The invention relates to new aminoaryl-1,3-oxazine-2,4-diones of the general formula (I)

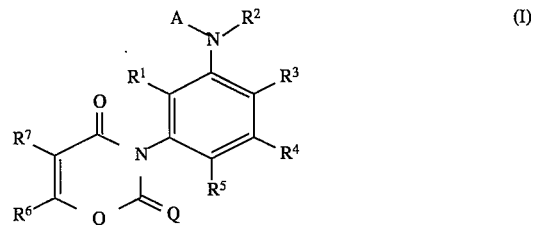

in which

A, Q, $R^1$, $R^2$, $R^3$, $R^4$, $R^5$, $R^6$ and $R^7$ have the meanings given in the description, to processes for their preparation, to new intermediates, and to their use as herbicides.

12 Claims, No Drawings

AMINOARYL-1,3-OXAZINE-2,4-DIONES

The invention relates to new aminoaryl-1,3-oxazine-2,4-diones, to processes for their preparation, to new intermediates, and to their use as herbicides.

It has already been disclosed that certain N-aryl-1,3-oxazine-2,4-diones, such as, for example, 3-(2-fluoro-4-chloro-5-chlorodifluoromethoxy-phenyl)-6,7-dihydro-cyclopent[e]-1,3-oxazine-2,4-(3H,5H)-dione, have herbicidal properties (cf. EP-A 371240; cf. also EP-A 529402).

However, the herbicidal activity of these known compounds is not satisfactory in all respects.

New aminoaryl-1,3-oxazine-2,4-diones of the general formula (I)

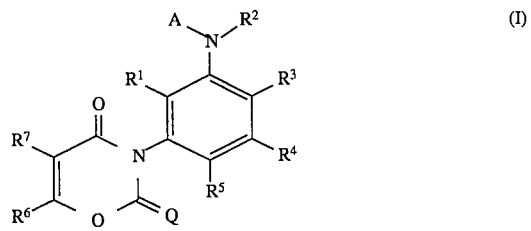

in which

A represents hydrogen or $C_1$–$C_6$-alkyl,

Q represents oxygen or sulphur, $R_1$ represents hydrogen or halogen, $R_2$ represents hydrogen, a radical from the series comprising $C_1$–$C_6$-alkyl, $C_2$–$C_6$-alkenyl, $C_2$–$C_6$-alkinyl, $C_1$–$C_6$-alkylcarbonyl, $C_1$–$C_6$-alkoxycarbonyl, $C_1$–$C_6$-alkylaminocarbonyl and $C_1$–$C_6$-alkylsulphonyl, each of which is optionally substituted by halogen or $C_1$–$C_4$-alkoxy, or represents di-($C_1$–$C_4$-alkyl)-aminosulphonyl, $R^2$ furthermore represents a radical from the series comprising phenyl, phenylcarbonyl, phenyl-$C_1$–$C_4$-alkyl, phenylsulphonyl or phenyl-$C_1$–$C_4$-alkylsulphonyl, each of which is optionally substituted by halogen, cyano, nitro, carboxyl, carbamoyl, $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (each of which is optionally substituted by halogen) or by $C_1$–$C_4$-alkoxycarbonyl, $R^3$ represents hydrogen, halogen, cyano, methyl, trifluoromethyl or methoxycarbonyl, $R^4$ represents hydrogen or halogen, $R^5$ represents hydrogen or halogen, $R^6$ represents hydrogen, halogen, or represents $C_1$–$C_4$-alkyl or phenyl, each of which is optionally substituted by halogen, and $R^7$ represents hydrogen, halogen, or represents $C_1$–$C_4$-alkyl or phenyl, each of which is optionally substituted by halogen, or together with $R^6$ represents $C_3$–$C_5$-alkanediyl, or together with $R^6$ forms a benzo group, have now been found.

The new aminoaryl-1,3-oxazine-2,4-diones of the general formula (I) are obtained when (a) nitroaryl-1,3-oxazine-2,4-diones of the general formula (II)

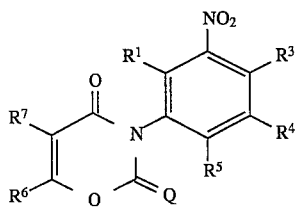

in which

Q, $R^1$, $R^3$, $R^4$, $R^5$, $R^6$ and $R^7$ have the abovementioned meanings, are reacted with a reducing agent, if appropriate in the presence of a catalyst or reaction auxiliary and if appropriate in the presence of a diluent, or when (b) aminoaryl-1,3-oxazine-2,4-diones of the general formula (Ia)

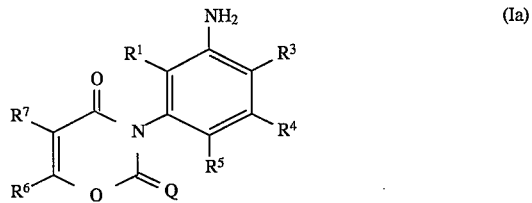

in which

Q, $R^1$, $R^3$, $R^4$, $R^5$, $R^6$ and $R^7$ have the abovementioned meanings, are reacted with electrophilic compounds of the general formula (III)

$$X^1 \text{—} A^1 \quad (III)$$

in which $A^1$ represents $C_1$–$C_6$-alkyl and $X^1$ represents halogen or the group —O—$SO_2$—O—$A^1$, and/or with electrophilic compounds of the general formula (IV)

$$X^2 \text{—} R^2 \quad (IV)$$

in which $R^2$ has the abovementioned meaning, with the exception of hydrogen, and $X^2$ represents halogen or the group

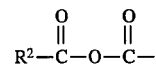

and/or, if appropriate, with isocyanates of the general formula (V)

$$O{=}C{=}N{=}R^8 \quad (V)$$

in which $R^8$ represents $C_1$–$C_6$-alkyl, if appropriate in the presence of an acid acceptor and if appropriate in the presence of a diluent, it being possible, if appropriate, for the sequence of the reaction with the compounds of the formulae (III) and/or (IV) and/or (V) to differ from the sequence indicated above.

The new aminoaryl-1,3-oxazine-2,4-diones of the general formula (I) are distinguished by a powerful herbicidal activity.

The invention preferably relates to compounds of the formula (I) in which

A represents hydrogen or $C_1$–$C_4$-alkyl,

Q represents oxygen or sulphur, $R^1$ represents hydrogen, fluorine, chlorine or bromine, $R^2$ represents hydrogen, a radical from the series comprising $C_1$–$C_4$-alkyl, $C_2$–$C_4$-alkenyl, $C_2$–$C_4$-alkinyl, $C_{1-C4}$-alkylcarbonyl, $C_1$–$C_4$-alkoxycarbonyl, $C_1$–$C_4$-alkylaminocarbonyl or $C_1$–$C_4$-alkylsulphonyl or di($C_1$–$C_3$-alkyl)aminosulphonyl, each of which is optionally substituted by fluorine, chlorine, methoxy or ethoxy, $R^2$ furthermore represents a radical from the series comprising phenyl, phenylcarbonyl, phenyl-$C_1$–$C_3$-alkyl, phenylsulphonyl or phenyl-$C_1$–$C_3$-alkylsulphonyl, each of which is optionally substituted by halogen, cyano, nitro, carboxyl, carbamoyl, $C_1$–$C_3$-alkyl, $C_1$–$C_3$-alkoxy, $C_1$–$C_3$-alkylthio, $C_1$–$C_3$-alkylsulphinyl, $C_1$–$C_3$-alkylsulphonyl (each of which is optionally substituted by fluorine and/or chlorine) or $C_1$–$C_3$-alkoxycarbonyl, $R^3$ represents hydrogen, fluorine, chlorine, bromine, cyano, methyl, trifluoromethyl or methoxycarbonyl, $R^4$ represents hydrogen, fluorine, chlorine or bromine, $R^5$ represents hydrogen, fluorine, chlorine or bromine, $R^6$ represents hydrogen, fluorine, chlorine, bromine, or represents $C_1$–$C_3$-alkyl or phenyl, each of which is optionally substituted by fluorine and/or chlorine, and $R^7$ represents hydrogen, fluorine, chlorine, bromine, or represents $C_1$–$C_3$-alkyl or phenyl, each of which is optionally substituted by fluorine and/or chlorine, or together with $R^6$ represents $C_3$–$C_4$-alkanediyl, or together with $R^6$ forms a benzo group.

The saturated or unsaturated hydrocarbon radicals mentioned in the definitions of the substituents, such as alkyl, alkenyl or alkinyl, are in each case straight-chain or branched, also in compounds which include hetero atoms, such as in alkoxy, alkylthio and the like.

Halogen generally represents fluorine, chlorine, bromine or iodine, preferably fluorine, chlorine or bromine.

The invention particularly relates to compounds of the formula (I) in which

A represents hydrogen, methyl, ethyl or n- or i-propyl,

Q represents oxygen or sulphur, $R^1$ represents hydrogen, $R^2$ represents hydrogen, methyl, ethyl, n- or i-propyl, allyl, propargyl, or represents acetyl or propionyl, each of which is optionally substituted by fluorine or chlorine, or represents methoxycarbonyl, ethoxycarbonyl, methylaminocarbonyl or ethylaminocarbonyl, or represents methylsulphonyl or ethylsulphonyl, each of which is optionally substituted by fluorine or chlorine, or represents dimethylaminosulphonyl, or represents phenyl, benzoyl, benzyl, phenylsulphonyl or phenylmethylsulphonyl, each of which is optionally substituted by fluorine, chlorine, cyano, nitro, carboxyl, methyl, trifluoromethyl, methoxy or methoxycarbonyl, $R^3$ represents chlorine, bromine or cyano, $R^4$ represents hydrogen, $R^5$ represents hydrogen, chlorine or fluorine, $R^6$ represents hydrogen, chlorine, bromine, methyl or trifluoromethyl and $R^7$ represents hydrogen, chlorine, bromine, methyl or trifluoromethyl, or together with $R^6$ represents trimethylene or tetramethylene.

Examples of the compounds of the formula (I) according to the invention are listed in Table 1 below.

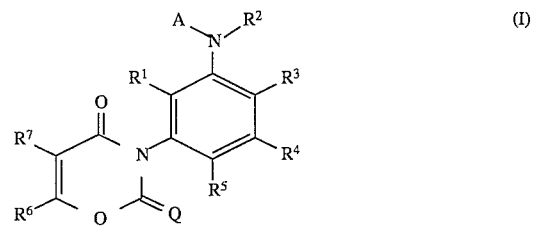
(I)

TABLE 1

Examples of the compounds of the formula (I) according to the invention

| $R^1$ | $R^2$ | $R^3$ | $R^4$ | $R^5$ | $R^6$ | $R^7$ | Q |
|---|---|---|---|---|---|---|---|
| H | $NH_2$ | Cl | H | H | $(CH_2)_3$ | | O |
| H | $NH_2$ | Cl | H | Cl | $(CH_2)_3$ | | O |
| H | $NH_2$ | Br | H | Cl | $(CH_2)_3$ | | O |
| H | $NH_2$ | Br | H | F | $(CH_2)_3$ | | O |
| H | $NH_2$ | $CH_3$ | H | F | $(CH_2)_3$ | | S |
| H | $NH_2$ | Cl | H | H | $(CH_2)_4$ | | O |
| H | $NH_2$ | Cl | H | Cl | $(CH_2)_4$ | | O |
| H | $NH_2$ | Br | H | H | $(CH_2)_4$ | | O |
| H | $NH_2$ | Br | H | F | $(CH_2)_4$ | | O |
| H | $NH_2$ | $CH_3$ | H | F | $(CH_2)_4$ | | O |
| H | $NH_2$ | Cl | H | Cl | $CH_2-C(CH_3)_2-CH_2-$ | | O |
| H | $NH_2$ | Cl | H | F | $CH_2-C(CH_3)_2-CH_2-$ | | O |
| H | $NH_2$ | Cl | H | F | $CH_2-CH(CH_3)-CH_2-$ | | O |
| H | $NH_2$ | Cl | H | F | $CH=CH-CH=CH-$ | | O |
| H | $NH_2$ | Cl | H | Cl | $CH=CH-CH=CH-$ | | O |
| H | $NH_2$ | Cl | H | Cl | $CH_3$ | H | O |
| H | $NH_2$ | Cl | H | Cl | $CH_3$ | $CH_3$ | O |
| H | $NH_2$ | Cl | H | F | $CH_3$ | $CH_3$ | O |
| H | $NH_2$ | Cl | H | Cl | $CH_3$ | $C_2H_5$ | O |

TABLE 1-continued

Examples of the compounds of the formula (I) according to the invention $$-N\begin{smallmatrix}A\\R^2\end{smallmatrix}$$ (with $R^1$)

| $R^1$ | $R^2$ | $R^3$ | $R^4$ | $R^5$ | $R^6$ | $R^7$ | Q |
|---|---|---|---|---|---|---|---|
| H | $NH_2$ | $CH_3$ | H | F | $CH_3$ | H | O |
| H | $NH_2$ | Cl | H | F | $CH_3$ | $CH_3$ | O |
| H | $NH_2$ | Cl | H | Cl | $CF_3$ | H | O |
| H | $NH_2$ | Cl | H | H | $CH_3$ | $CH_3$ | O |
| H | $NH_2$ | Cl | H | F | $CF_3$ | H | O |
| H | $NH_2$ | Cl | H | H | $CF_3$ | H | O |
| H | $NH_2$ | Cl | H | F | $CF_3$ | $CH_3$ | O |
| H | $NH_2$ | Br | H | F | $CH_3$ | $CH_3$ | O |
| H | $NH_2$ | F | H | F | $CH_3$ | $C_2H_5$ | O |
| H | $NH_2$ | Cl | H | F | H | $CF_3$ | O |
| H | $NH_2$ | Cl | H | F | H | F | O |
| H | $NH_2$ | Cl | H | F | $CF_3$ | $CF_3$ | O |
| H | $NHSO_2CH_3$ | Cl | H | H | $(CH_2)_3$ | | O |
| H | $NHSO_2CF_3$ | Cl | H | F | $(CH_2)_3$ | | O |
| H | $NHSO_2C_2H_5$ | Cl | H | Cl | $(CH_2)_3$ | | O |
| H | $NHSO_2C_3H_7$ | Br | H | Cl | $(CH_2)_3$ | | O |
| H | $N(CH_3)SO_2CH_3$ | Br | H | F | $(CH_2)_3$ | | O |
| H | $NHSO_2CH_2C_6H_5$ | $CH_3$ | H | H | $(CH_2)_3$ | | S |
| H | $NHSO_2CH_3$ | Cl | H | H | $(CH_2)_4$ | | O |
| H | $NHSO_2C_4H_9$ | Cl | H | Cl | $(CH_2)_4$ | | O |
| H | $NHSO_2C_3H_6Cl$ | Cl | H | F | $(CH_2)_4$ | | O |
| H | $NHSO_2CH_3$ | Br | H | H | $(CH_2)_4$ | | O |
| H | $NHSO_2C_6H_5$ | $CH_3$ | H | F | $(CH_2)_4$ | | O |
| H | $N(SO_2CH_3)_2$ | Br | H | Cl | $(CH_2)_4$ | | O |
| H | $NHSO_2CH_3$ | Cl | H | Cl | $CH_2-C(CH_3)_2-CH_2-$ | | O |
| H | $N(CH_3)SO_2C_2H_5$ | Cl | H | F | $CH_2-C(CH_3)_2-CH_2-$ | | O |
| H | $NHSO_2C_3H_7$ | Cl | H | F | $CH_2-CH(CH_3)-CH_2-$ | | O |
| H | $NHSO_2C_3H_6Cl$ | Cl | H | F | $CH_2=CH-CH=CH-$ | | O |
| H | $NHSO_2CH_3$ | Cl | H | F | $CH=CH-CH=CH-$ | | O |
| H | $NHSO_2C_2H_5$ | Cl | H | Cl | $CH=CH-CH=CH-$ | | O |
| H | $NHSO_2CH_3$ | Cl | H | Cl | $CH_3$ | H | O |
| H | $NHSO_2C_2H_5$ | Cl | H | Cl | $CH_3$ | $CH_3$ | O |
| H | $NHSO_2C_3H_7$ | Cl | H | Cl | $CH_3$ | $C_2H_5$ | O |
| H | $N(SO_2CH_3)_2$ | Cl | H | F | $CH_3$ | H | O |
| H | $NHSO_2CH_3$ | Cl | H | F | $CH_3$ | $CH_3$ | O |
| H | $NHSO_2CH_3$ | Cl | H | Cl | $CF_3$ | H | O |
| H | $NHSO_2CH_3$ | Cl | H | H | $CH_3$ | $CH_3$ | O |
| H | $NHSO_2CH_3$ | Cl | H | F | $CF_3$ | H | O |
| H | $NHSO_2C_2H_5$ | Cl | H | F | $CF_3$ | H | O |
| H | $NHSO_2CH_3$ | Cl | H | H | $CF_3$ | H | O |
| H | $NH(CH_3)$ | Cl | H | H | $(CH_2)_3$ | | O |
| H | $NHCOOCH_3$ | Cl | H | Cl | $(CH_2)_3$ | | O |
| H | $NHCOC_6H_5$ | Br | H | Cl | $(CH_2)_3$ | | O |
| H | $N(CH_3)_2$ | $CH_3$ | H | F | $(CH_2)_3$ | | O |
| H | $NHCONHCH_3$ | Br | H | H | $(CH_2)_3$ | | S |
| H | $NHCONHC_6H_5$ | Cl | H | H | $(CH_2)_4$ | | O |
| H | $NHCOOC_2H_5$ | Cl | H | Cl | $(CH_2)_4$ | | O |
| H | $NHCOCH_3$ | Br | H | H | $(CH_2)_4$ | | O |
| H | $NHCOCF_3$ | Cl | H | F | $(CH_2)_4$ | | O |
| H | $NHC_2H_5$ | Br | H | F | $(CH_2)_4$ | | O |
| H | $NHCOOCH_3$ | $CH_3$ | H | F | $(CH_2)_4$ | | O |
| H | $NHCONHC_2H_5$ | Cl | H | Cl | $CH_2-C(CH_3)_2-CH_2-$ | | O |
| H | $N(CH_3)(COOCH_3)$ | Cl | H | F | $CH_2-C(CH_3)_2-CH_2-$ | | O |
| H | $N(CH_3)(COOC_2H_5)$ | Cl | H | F | $CH_2-CH(CH_3)-CH_2-$ | | O |
| H | $NHCOOC_3H_7$ | Cl | H | F | $CH=CH-CH=CH-$ | | O |
| H | $NHCON(CH_3)_2$ | Cl | H | Cl | $CH=CH-CH=CH-$ | | O |
| H | $NHCOOCH_3$ | Cl | H | Cl | $CH_3$ | H | O |
| H | $NHC_2H_5$ | Cl | H | Cl | $CH_3$ | $CH_3$ | O |
| H | $NHCOOC_4H_9$ | Cl | H | Cl | $CH_3$ | $C_2H_5$ | O |
| H | $NHCOCH_3$ | $CH_3$ | H | F | $CH_3$ | H | O |
| H | $NHCOOCH_3$ | Cl | H | F | $CH_3$ | $CH_3$ | O |
| H | $NHCOOC_2H_5$ | Cl | H | Cl | $CF_3$ | H | O |
| H | $NHCOC_2H_5$ | Cl | H | H | $CH_3$ | $CH_3$ | O |
| H | $NHCONHCH_3$ | Cl | H | F | $CF_3$ | H | O |
| H | $NHCOOCH_3$ | Cl | H | H | $CF_3$ | H | O |
| H | $NHCOOC_2H_5$ | Cl | H | F | $CF_3$ | $CH_3$ | O |
| H | $N(CH_3)COOCH_3$ | Br | H | F | $CH_3$ | $CH_3$ | O |
| H | $NHCOC_6H_5$ | F | H | F | $CH_3$ | $C_2H_5$ | O |
| H | $NHCOOC_2H_5$ | Cl | H | F | H | $CF_3$ | O |

TABLE 1-continued

Examples of the compounds of the formula (I) according to the invention $$-N\begin{matrix}A\\R^2\end{matrix}$$

| R¹ | R² | R³ | R⁴ | R⁵ | R⁶ | R⁷ | Q |
|---|---|---|---|---|---|---|---|
| H | NHCH₃ | Cl | H | F | CF₃ | CF₃ | O |
| H | NHC₂H₅ | Cl | H | F | CH₃ | CH₃ | S |
| H | NHCOOCH₃ | Cl | H | H | CH₃ | CF₃ | O |
| H | NHCOOC₂H₅ | Cl | H | F | CH₃ | CF₃ | O |
| H | NHCONHCH₃ | Cl | H | Cl | CH₃ | CF₃ | O |
| H | NH₂ | CN | H | Cl | CH₃ | H | O |
| H | NH₂ | CN | H | Cl | CH₃ | CH₃ | O |
| H | NH₂ | CN | H | F | CH₃ | CH₃ | O |
| H | NH₂ | CN | H | Cl | CH₃ | C₂H₅ | O |
| H | NH₂ | CN | H | F | CH₃ | H | O |
| H | NH₂ | CN | H | F | CH₃ | CH₃ | O |
| H | NH₂ | CN | H | Cl | CF₃ | H | O |
| H | NH₂ | CN | H | H | CH₃ | CH₃ | O |
| H | NH₂ | CN | H | F | CF₃ | H | O |
| H | NH₂ | CN | H | H | CF₃ | H | O |
| H | NH₂ | CN | H | F | CF₃ | CH₃ | O |
| H | NH₂ | CN | H | F | CH₃ | CH₃ | O |
| H | NH₂ | CN | H | F | CH₃ | C₂H₅ | O |
| H | NH₂ | CN | H | H | H | CF₃ | O |
| H | NH₂ | CN | H | F | H | CF₃ | O |
| H | NH₂ | CN | H | F | CF₃ | CF₃ | O |
| H | NH₂ | CN | H | F | CH₃ | CH₃ | S |
| H | NH₂ | CN | H | H | CH₃ | CF₃ | O |
| H | NH₂ | CN | H | F | CH₃ | CF₃ | O |
| H | NH₂ | CN | H | Cl | CH₃ | CF₃ | O |
| H | NH₂ | CN | H | H | (CH₂)₃ | | O |
| H | NH₂ | CN | H | Cl | (CH₂)₃ | | O |
| H | NH₂ | CN | H | Cl | (CH₂)₃ | | O |
| H | NH₂ | CN | H | F | (CH₂)₃ | | O |
| H | NH₂ | COOCH₃ | H | F | (CH₂)₃ | | S |
| H | NH₂ | CN | H | H | (CH₂)₄ | | O |
| H | NH₂ | CN | H | Cl | (CH₂)₄ | | O |
| H | NH₂ | CN | H | H | (CH₂)₄ | | O |
| H | NH₂ | CN | H | F | (CH₂)₄ | | O |
| H | NH₂ | CN | H | F | (CH₂)₅ | | O |
| H | NH₂ | CN | H | Cl | CH₂—C(CH₃)₂—CH₂— | | O |
| H | NH₂ | CN | H | F | CH₂—C(CH₃)₂—CH₂— | | O |
| H | NH₂ | CN | H | F | CH₂—CH(CH₃)—CH₂— | | O |
| H | NH₂ | CN | H | F | CH=CH—CH=CH— | | O |
| H | NH₂ | CN | H | Cl | CH=CH—CH=CH— | | O |
| H | NHSO₂CH₃ | CN | H | Cl | CH₃ | H | O |
| H | NHSO₂C₂H₅ | CN | H | Cl | CH₃ | CH₃ | O |
| H | NHSO₂CH₂CF₃ | CN | H | Cl | CH₃ | CH₃ | O |
| H | NHSO₂C₃H₇ | CN | H | Cl | CH₃ | C₂H₅ | O |
| H | N(SO₂CH₃)₂ | CN | H | F | CH₃ | H | O |
| H | NHSO₂CH₃ | CN | H | F | CH₃ | CH₃ | O |
| H | NHSO₂CH₃ | CN | H | Cl | CF₃ | H | O |
| H | NHSO₂CH₃ | CN | H | H | CH₃ | CH₃ | O |
| H | NHSO₂CH₃ | CN | H | F | CF₃ | H | O |
| H | NHSO₂C₂H₅ | CN | H | F | CF₃ | H | O |
| H | NHSO₂C₃H₇ | CN | H | F | CF₃ | H | O |
| H | NHSO₂CH₃ | CN | H | H | CF₃ | H | O |
| H | NHSO₂CH₃ | CN | H | F | CF₃ | CH₃ | O |
| H | NHSO₂C₂H₅ | CN | H | F | CH₃ | CH₃ | O |
| H | NHSO₂C₄H₉ | CN | H | F | CH₃ | C₂H₅ | O |
| H | NHSO₂CH₃ | CN | H | F | H | CF₃ | O |
| H | NHSO₂C₂H₅ | CN | H | F | H | CF₃ | O |
| H | NHSO₂C₃H₇ | CN | H | F | CF₃ | CF₃ | O |
| H | N(CH₃)SO₂CH₃ | CN | H | F | CH₃ | CH₃ | S |
| H | NHSO₂CH₃ | CN | H | H | CH₃ | CF₃ | O |
| H | NHSO₂C₂H₅ | CN | H | F | CH₃ | CF₃ | O |
| H | NHSO₂C₄H₉ | CN | H | Cl | CH₃ | CF₃ | O |
| H | NHSO₂CH₃ | CN | H | H | (CH₂)₃ | | O |
| H | NHSO₂CH₃ | CN | H | F | (CH₂)₃ | | O |
| H | NHSO₂C₂H₅ | CN | H | Cl | (CH₂)₃ | | O |
| H | NHSO₂C₃H₇ | CN | H | Cl | (CH₂)₃ | | O |
| H | N(CH₃)SO₂CH₃ | CN | H | F | (CH₂)₃ | | O |
| H | NHSO₂CF₃ | CN | H | F | (CH₂)₃ | | O |
| H | NHSO₂CH₂C₆H₅ | CN | H | H | (CH₂)₃ | | S |

TABLE 1-continued

Examples of the compounds of the formula (I) according to the invention $$-N\begin{smallmatrix}A\\R^2\end{smallmatrix}$$

| R¹ | R² | R³ | R⁴ | R⁵ | R⁶ | R⁷ | Q |
|---|---|---|---|---|---|---|---|
| H | NHSO₂CH₃ | CN | H | H | (CH₂)₄ | | O |
| H | NHSO₂CH₃ | CN | H | F | (CH₂)₄ | | O |
| H | NHSO₂C₄H₉ | CN | H | Cl | (CH₂)₄ | | O |
| H | NHSO₂CH₃ | CN | H | H | (CH₂)₄ | | O |
| H | NHSO₂C₆H₅ | CN | H | F | (CH₂)₄ | | O |
| H | N(SO₂CH₃)₂ | CN | H | Cl | (CH₂)₄ | | O |
| H | NHSO₂CH₃ | CN | H | Cl | CH₂—C(CH₃)₂—CH₂— | | O |
| H | N(CH₃)SO₂C₂H₅ | CN | H | F | CH₂—C(CH₃)₂—CH₂— | | O |
| H | NHSO₂C₃H₇ | CN | H | F | CH₂—CH(CH₃)—CH₂— | | O |
| H | NHSO₂CH₃ | CN | H | F | CH=CH—CH=CH— | | O |
| H | NHSO₂C₂H₅ | CN | H | Cl | CH=CH—CH=CH— | | O |
| H | NH(CH₃) | CN | H | H | (CH₂)₃ | | O |
| H | NHCOOCH₃ | CN | H | Cl | (CH₂)₃ | | O |
| H | NHCOOC₂H₅ | CN | H | F | (CH₂)₃ | | O |
| H | NHCOC₆H₅ | CN | H | Cl | (CH₂)₃ | | O |
| H | N(CH₃)₂ | CN | H | F | (CH₂)₃ | | O |
| H | NHCONHCH₃ | CN | H | H | (CH₂)₃ | | S |
| H | NHCONHC₆H₅ | CN | H | H | (CH₂)₄ | | O |
| H | NHCOOC₂H₅ | CN | H | Cl | (CH₂)₄ | | O |
| H | NHCOOCH₃ | CN | H | F | (CH₂)₄ | | O |
| H | NHCOCH₃ | CN | H | H | (CH₂)₄ | | O |
| H | NHC₂H₅ | CN | H | F | (CH₂)₄ | | O |
| H | NHCOOCH₃ | CN | H | F | (CH₂)₄ | | O |
| H | NHCONHC₂H₅ | CN | H | Cl | CH₂—C(CH₃)₂—CH₂— | | O |
| H | N(CH₃)(COOCH₃) | CN | H | F | CH₂—C(CH₃)₂—CH₂— | | O |
| H | N(CH₃)(COOC₂H₅) | CN | H | F | CH₂—CH(CH₃)—CH₂— | | O |
| H | NHCOOC₃H₇ | CN | H | F | CH=CH—CH=CH— | | O |
| H | NHCON(CH₃)₂ | CN | H | Cl | CH=CH—CH=CH— | | O |
| H | NHCOOCH₃ | CN | H | Cl | CH₃ | H | O |
| H | NHC₂H₅ | CN | H | Cl | CH₃ | CH₃ | O |
| H | NHCOOC₄H₉ | CN | H | Cl | CH₃ | C₂H₅ | O |
| H | NHCOCH₃ | CN | H | F | CH₃ | H | O |
| H | NHCOOCH₃ | CN | H | F | CH₃ | CH₃ | O |
| H | NHCOOC₂H₅ | CN | H | F | CF₃ | H | O |
| H | NHCOOC₂H₅ | CN | H | Cl | CF₃ | H | O |
| H | NHCOC₂H₅ | CN | H | H | CH₃ | CH₃ | O |
| H | NHCONHCH₃ | CN | H | F | CF₃ | H | O |
| H | NHCOOCH₃ | CN | H | H | CF₃ | H | O |
| H | NHCOOC₂H₅ | CN | H | F | CF₃ | CH₃ | O |
| H | N(CH₃)COOCH₃ | CN | H | F | CH₃ | CH₃ | O |
| H | NHCOC₆H₅ | CN | H | F | CH₃ | C₂H₅ | O |
| H | NHCOCH₃ | CN | H | F | H | CF₃ | O |
| H | NHCOOC₂H₅ | CN | H | F | H | CF₃ | O |
| H | NHCH₃ | CN | H | F | CF₃ | CF₃ | O |
| H | NHC₂H₅ | CN | H | F | CH₃ | CH₃ | S |
| H | NHCOOC₂H₅ | CN | H | H | CH₃ | CF₃ | O |
| H | NHCOCH₃ | CN | H | F | CH₃ | CF₃ | O |
| H | NHCONHCH₃ | CN | H | Cl | CH₃ | CF₃ | O |
| H | NH₂ | CN | H | H | (CH₂)₃ | | O |
| H | NH₂ | CN | H | Cl | (CH₂)₃ | | O |
| H | NH₂ | CN | H | Cl | (CH₂)₃ | | O |
| H | NH₂ | CN | H | F | (CH₂)₃ | | O |
| H | NH₂ | COOCH₃ | H | F | (CH₂)₃ | | S |
| H | NH₂ | CN | H | H | (CH₂)₄ | | O |
| H | NH₂ | CN | H | Cl | (CH₂)₄ | | O |
| H | NH₂ | CN | H | H | (CH₂)₄ | | O |
| H | NH₂ | CN | H | F | (CH₂)₄ | | O |
| H | NH₂ | CN | H | F | (CH₂)₅ | | O |
| H | NH₂ | CN | H | Cl | CH₂—C(CH₃)₂—CH₂— | | O |
| H | NH₂ | CN | H | F | CH₂—C(CH₃)₂—CH₂— | | O |
| H | NH₂ | CN | H | F | CH₂—CH(CH₃)—CH₂— | | O |
| H | NH₂ | CN | H | F | CH=CH—CH=CH— | | O |
| H | NH₂ | CN | H | Cl | CH=CH—CH=CH— | | O |
| H | NHSO₂CH₃ | CN | H | Cl | CH₃ | H | O |
| H | NHSO₂C₂H₅ | CN | H | Cl | CH₃ | CH₃ | O |
| H | NHSO₂CH₂CF₃ | CN | H | Cl | CH₃ | CH₃ | O |
| H | NHSO₂C₃H₇ | CN | H | Cl | CH₃ | C₂H₅ | O |
| H | N(SO₂CH₃)₂ | CN | H | F | CH₃ | H | O |
| H | NHSO₂CH₃ | CN | H | F | CH₃ | CH₃ | O |

TABLE 1-continued

Examples of the compounds of the formula (I)
according to the invention

| R¹ | R² | R³ | R⁴ | R⁵ | R⁶ | R⁷ | Q |
|---|---|---|---|---|---|---|---|
| H | NHSO$_2$CH$_3$ | CN | H | Cl | CF$_3$ | H | O |
| H | NHSO$_2$CH$_3$ | CN | H | H | CH$_3$ | CH$_3$ | O |
| H | NHSO$_2$CH$_3$ | CN | H | F | CF$_3$ | H | O |
| H | NHSO$_2$C$_2$H$_5$ | CN | H | F | CF$_3$ | H | O |
| H | NHSO$_2$C$_3$H$_7$ | CN | H | F | CF$_3$ | H | O |
| H | NHSO$_2$CH$_3$ | CN | H | H | CF$_3$ | H | O |
| H | NHSO$_2$CH$_3$ | CN | H | F | CF$_3$ | CH$_3$ | O |
| H | NHSO$_2$C$_2$H$_5$ | CN | H | F | CH$_3$ | CH$_3$ | O |
| H | NHSO$_2$C$_4$H$_9$ | CN | H | F | CH$_3$ | C$_2$H$_5$ | O |
| H | NHSO$_2$CH$_3$ | CN | H | F | H | CF$_3$ | O |
| H | NHSO$_2$C$_2$H$_5$ | CN | H | F | H | CF$_3$ | O |
| H | NHSO$_2$C$_3$H$_7$ | CN | H | F | CF$_3$ | CF$_3$ | O |
| H | N(CH$_3$)SO$_2$CH$_3$ | CN | H | F | CH$_3$ | CH$_3$ | S |
| H | NHSO$_2$CH$_3$ | CN | H | H | CH$_3$ | CF$_3$ | O |
| H | NHSO$_2$C$_2$H$_5$ | CN | H | F | CH$_3$ | CF$_3$ | O |
| H | NHSO$_2$C$_4$H$_9$ | CN | H | Cl | CH$_3$ | CF$_3$ | O |
| H | NHSO$_2$CH$_3$ | CN | H | H | (CH$_2$)$_3$ | | O |
| H | NHSO$_2$CH$_3$ | CN | H | F | (CH$_2$)$_3$ | | O |
| H | NHSO$_2$C$_2$H$_5$ | CN | H | Cl | (CH$_2$)$_3$ | | O |
| H | NHSO$_2$C$_3$H$_7$ | CN | H | Cl | (CH$_2$)$_3$ | | O |
| H | N(CH$_3$)SO$_2$CH$_3$ | CN | H | F | (CH$_2$)$_3$ | | O |
| H | NHSO$_2$CF$_3$ | CN | H | F | (CH$_2$)$_3$ | | O |
| H | NHSO$_2$CH$_2$C$_6$H$_5$ | CN | H | H | (CH$_2$)$_3$ | | S |
| H | NHSO$_2$CH$_3$ | CN | H | H | (CH$_2$)$_4$ | | O |
| H | NHSO$_2$CH$_3$ | CN | H | F | (CH$_2$)$_4$ | | O |
| H | NHSO$_2$C$_4$H$_9$ | CN | H | Cl | (CH$_2$)$_4$ | | O |
| H | NHSO$_2$CH$_3$ | CN | H | H | (CH$_2$)$_4$ | | O |
| H | NHSO$_2$C$_6$H$_5$ | CN | H | F | (CH$_2$)$_4$ | | O |
| H | N(SO$_2$CH$_3$)$_2$ | CN | H | Cl | (CH$_2$)$_4$ | | O |
| H | NHSO$_2$CH$_3$ | CN | H | Cl | CH$_2$—C(CH$_3$)$_2$—CH$_2$— | | O |
| H | N(CH$_3$)SO$_2$C$_2$H$_5$ | CN | H | F | CH$_2$—C(CH$_3$)$_2$—CH$_2$— | | O |
| H | NHSO$_2$C$_3$H$_7$ | CN | H | F | CH$_2$—CH(CH$_3$)—CH$_2$— | | O |
| H | NHSO$_2$CH$_3$ | CN | H | F | CH=CH—CH=CH— | | O |
| H | NHSO$_2$C$_2$H$_5$ | CN | H | Cl | CH=CH—CH=CH— | | O |
| H | NH(CH$_3$) | CN | H | H | (CH$_2$)$_3$ | | O |
| H | NHCOOCH$_3$ | CN | H | Cl | (CH$_2$)$_3$ | | O |
| H | NHCOOC$_2$H$_5$ | CN | H | F | (CH$_2$)$_3$ | | O |
| H | NHCOC$_6$H$_5$ | CN | H | Cl | (CH$_2$)$_3$ | | O |
| H | N(CH$_3$)$_2$ | CN | H | F | (CH$_2$)$_3$ | | O |
| H | NHCONHCH$_3$ | CN | H | H | (CH$_2$)$_3$ | | S |
| H | NHCONHC$_6$H$_5$ | CN | H | H | (CH$_2$)$_4$ | | O |
| H | NHCOOC$_2$H$_5$ | CN | H | Cl | (CH$_2$)$_4$ | | O |
| H | NHCOOCH$_3$ | CN | H | F | (CH$_2$)$_4$ | | O |
| H | NHCOCH$_3$ | CN | H | H | (CH$_2$)$_4$ | | O |
| H | NHC$_2$H$_5$ | CN | H | F | (CH$_2$)$_4$ | | O |
| H | NHCOOCH$_3$ | CN | H | F | (CH$_2$)$_4$ | | O |
| H | NHCONHC$_2$H$_5$ | CN | H | Cl | CH$_2$—C(CH$_3$)$_2$—CH$_2$— | | O |
| H | N(CH$_3$)(COOCH$_3$) | CN | H | F | CH$_2$—C(CH$_3$)$_2$—CH$_2$— | | O |
| H | N(CH$_3$)(COOC$_2$H$_5$) | CN | H | F | CH$_2$—CH(CH$_3$)—CH$_2$— | | O |
| H | NHCOOC$_3$H$_7$ | CN | H | F | CH=CH—CH=CH— | | O |
| H | NHCON(CH$_3$)$_2$ | CN | H | Cl | CH=CH—CH=CH— | | O |
| H | NHCOOCH$_3$ | CN | H | Cl | CH$_3$ | H | O |
| H | NHC$_2$H$_5$ | CN | H | Cl | CH$_3$ | CH$_3$ | O |
| H | NHCOOC$_4$H$_9$ | CN | H | Cl | CH$_3$ | C$_2$H$_5$ | O |
| H | NHCOCH$_3$ | CN | H | F | CH$_3$ | H | O |
| H | NHCOOCH$_3$ | CN | H | F | CH$_3$ | CH$_3$ | O |
| H | NHCOOC$_2$H$_5$ | CN | H | F | CF$_3$ | H | O |
| H | NHCOOC$_2$H$_5$ | CN | H | Cl | CF$_3$ | H | O |
| H | NHCOC$_2$H$_5$ | CN | H | H | CH$_3$ | CH$_3$ | O |
| H | NHCONHCH$_3$ | CN | H | F | CF$_3$ | H | O |
| H | NHCOOCH$_3$ | CN | H | H | CF$_3$ | H | O |
| H | NHCOOC$_2$H$_5$ | CN | H | F | CF$_3$ | CH$_3$ | O |
| H | N(CH$_3$)COOCH$_3$ | CN | H | F | CH$_3$ | CH$_3$ | O |
| H | NHCOC$_6$H$_5$ | CN | H | F | CH$_3$ | C$_2$H$_5$ | O |
| H | NHCOCH$_3$ | CN | H | F | H | CF$_3$ | O |
| H | NHCOOC$_2$H$_5$ | CN | H | F | H | CF$_3$ | O |
| H | NHCH$_3$ | CN | H | F | CF$_3$ | CF$_3$ | O |
| H | NHC$_2$H$_5$ | CN | H | F | CH$_3$ | CH$_3$ | S |
| H | NHCOOC$_2$H$_5$ | CN | H | H | CH$_3$ | CF$_3$ | O |

TABLE 1-continued

Examples of the compounds of the formula (I) according to the invention

| R¹ | -N(A)(R²) | R³ | R⁴ | R⁵ | R⁶ | R⁷ | Q |
|---|---|---|---|---|---|---|---|
| H | NHCOCH₃ | CN | H | F | CH₃ | CF₃ | O |
| H | NHCONHCH₃ | CN | H | Cl | CH₃ | CF₃ | O |

If, for example, 3-(4-chloro-2-fluoro-5-nitrophenyl)-6-methyl-5-trifluoromethyl-1,3-oxazine-2,4(3H,5H)-dione and iron are used as starting substances in process (a) according to the invention in the presence of acetic acid, the course of the reaction can be represented by the following equation:

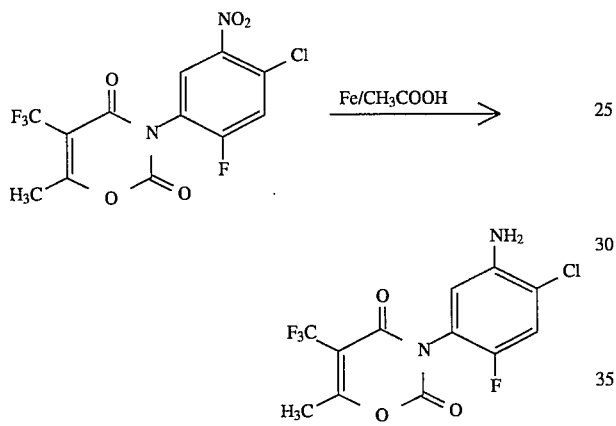

If, for example, 3-(4-bromo-2-fluoro-5-nitrophenyl)-benzo[e]-1,3-oxazine-2,4(3H,5H)-dione and hydrogen are used as starting substances in process (a) according to the invention, the course of the reaction can be represented by the following equation:

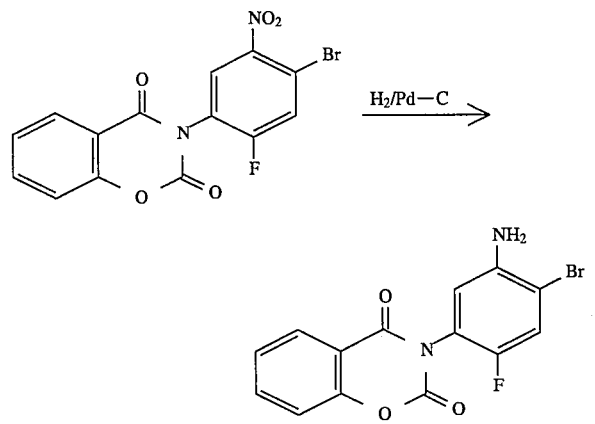

If, for example, 3-(5-amino-2-chloro-4-cyanophenyl)-5-chloro-6-methyl-1,3-oxazine-2,4(3H,5H)-dione and butanesulphonyl chloride are used as starting substances in process (b) according to the invention, the course of the reaction can be represented by the following equation:

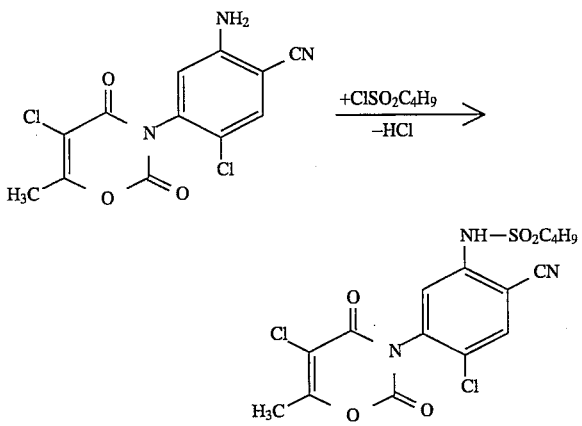

Formula (II) provides a general definition of the nitroaryl-1,3-oxazine-2,4-diones to be used as starting substances in process (a) according to the invention for the preparation of compounds of the formula (I).

In formula (II), Q, R¹, R³, R⁴, R⁵, R⁶ and R⁷ preferably, or in particular, have those meanings which have already been mentioned above in connection with the description of the compounds of the formula (I) according to the invention as being preferred, or particularly preferred, for Q, R¹, R³, R⁴, R⁵, R⁶ and R⁷.

Examples of the starting substances of the formula (II) are listed in Table 2 below.

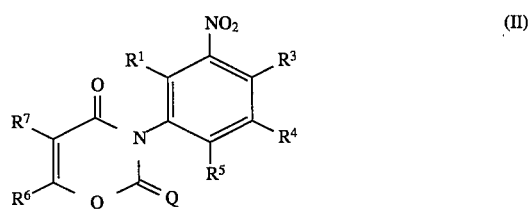

TABLE 2

Examples of the compounds of the formula (II) according to the invention

| R¹ | R³ | R⁴ | R⁵ | R⁶ | R⁷ | Q |
|---|---|---|---|---|---|---|
| H | Cl | H | H | (CH₂)₃ | | O |
| H | Cl | H | Cl | (CH₂)₃ | | O |
| H | Br | H | Cl | (CH₂)₃ | | O |
| H | Br | H | F | (CH₂)₃ | | O |
| H | CH₃ | H | H | (CH₂)₃ | | O |
| H | Cl | H | H | (CH₂)₄ | | O |
| H | Cl | H | Cl | (CH₂)₄ | | O |
| H | Br | H | H | (CH₂)₄ | | O |
| H | Br | H | F | (CH₂)₄ | | O |

TABLE 2-continued

Examples of the compounds of the formula (II) according to the invention

| $R^1$ | $R^3$ | $R^4$ | $R^5$ | $R^6$ | $R^7$ | Q |
|---|---|---|---|---|---|---|
| H | $CH_3$ | H | Cl | $(CH_2)_4$ | | O |
| H | Cl | H | Cl | $CH_2-C(CH_3)_2-CH_2-$ | | O |
| H | Cl | H | F | $CH_2-C(CH_3)_2-CH_2-$ | | O |
| H | Cl | H | F | $CH_2-CH(CH_3)-CH_2-$ | | O |
| H | Cl | H | F | $CH=CH-CH=CH-$ | | O |
| H | Cl | H | Cl | $CH=CH-CH=CH-$ | | O |
| H | Cl | H | Cl | $CH_3$ | H | O |
| H | Cl | H | Cl | $CH_3$ | $CH_3$ | O |
| H | Cl | H | Cl | $CH_3$ | $C_2H_5$ | O |
| H | $CH_3$ | H | F | $CH_3$ | H | O |
| H | Cl | H | F | $CH_3$ | $CH_3$ | O |
| H | Cl | H | Cl | $CF_3$ | H | O |
| H | Cl | H | H | $CH_3$ | $CH_3$ | O |
| H | Cl | H | F | $CF_3$ | H | O |
| H | Cl | H | H | $CF_3$ | H | O |
| H | Cl | H | F | $CF_3$ | $CH_3$ | O |
| H | Br | H | F | $CH_3$ | $CH_3$ | O |
| H | F | H | F | $CH_3$ | $C_2H_5$ | O |
| H | Cl | H | F | H | $CF_3$ | O |
| H | Cl | H | F | $CH_3$ | $CF_3$ | O |
| H | Cl | H | F | $CF_3$ | $CF_3$ | O |
| H | Cl | H | H | $CH_3$ | $CF_3$ | O |
| H | Cl | H | F | $CH_3$ | $CH_3$ | S |
| H | CN | H | H | $(CH_2)_3$ | | O |
| H | CN | H | Cl | $(CH_2)_3$ | | O |
| H | CN | H | Cl | $(CH_2)_3$ | | O |
| H | CN | H | F | $(CH_2)_3$ | | S |
| H | CN | H | H | $(CH_2)_3$ | | S |
| H | CN | H | H | $(CH_2)_4$ | | S |
| H | N | H | Cl | $(CH_2)_4$ | | S |
| H | CN | H | H | $(CH_2)_4$ | | O |
| H | CN | H | F | $(CH_2)_4$ | | O |
| H | CN | H | Cl | $(CH_2)_4$ | | O |
| H | CN | H | Cl | $CH_2-C(CH_3)_2-CH_2-$ | | O |
| H | CN | H | F | $CH_2-C(CH_3)_2-CH_2-$ | | O |
| H | CN | H | F | $CH_2-CH(CH_3)-CH_2-$ | | O |
| H | CN | H | F | $CH=CH-CH=CH-$ | | O |
| H | CN | H | Cl | $CH=CH-CH=CH-$ | | O |
| H | CN | H | H | $CH=CH-CH=CH-$ | | O |
| H | CN | H | Cl | $CH_3$ | H | O |
| H | CN | H | H | $CH_3$ | $CH_3$ | O |
| H | CN | H | Cl | $CH_3$ | $CH_3$ | O |
| H | CN | H | F | $CH_3$ | $CH_3$ | O |
| H | CN | H | Cl | $CH_3$ | $C_2H_5$ | O |
| H | CN | H | F | $CH_3$ | H | O |
| H | CN | H | F | $CH_3$ | $CH_3$ | O |
| H | CN | H | Cl | $CF_3$ | H | O |
| H | CN | H | H | $CH_3$ | $CH_3$ | O |
| H | CN | H | F | $CF_3$ | H | O |
| H | CN | H | H | $CF_3$ | H | O |
| H | CN | H | F | $CF_3$ | $CH_3$ | O |
| H | CN | H | F | $CH_3$ | $CH_3$ | O |
| H | CN | H | F | $CH_3$ | $C_2H_5$ | O |
| H | CN | H | F | H | $CF_3$ | O |
| H | CN | H | F | $CH_3$ | $CF_3$ | O |
| H | CN | H | F | $CF_3$ | $CF_3$ | O |
| H | CN | H | H | $CH_3$ | $CF_3$ | O |
| H | CN | H | F | $CH_3$ | $CH_3$ | S |

The nitroaryl-1,3-oxazine-2,4-diones of the formula (II) were hitherto not known from the literature; as new substances, they are part of the present patent application.

The new compounds of the formula (II) are obtained when aryl iso(thio)cyanates of the general formula (VI)

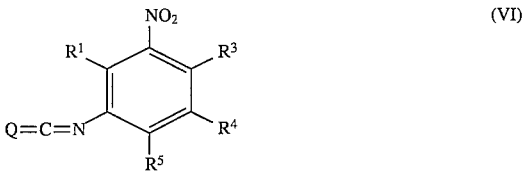

(VI)

in which

Q, $R^1$, $R^3$, $R^4$, and have the abovementioned meanings, (α) are reacted with 1,3-dioxin-4-ones of the general formula (VII)

(VII)

in which $R^6$ and $R^7$ have the abovementioned meanings and $R^8$ and $R^9$ represent hydrogen or optionally substituted alkyl, if appropriate in the presence of a diluent, or (β) are reacted with dicarbonyl dichlorides of the general formula (VIII)

(VIII)

in which $R^7$ has the abovementioned meaning, if appropriate in the presence of a diluent, or (γ) are reacted with 2-diazo-1,3-diketones of the general formula (IX)

(IX)

in which $R^6$ and $R^7$ have the abovementioned meanings, if appropriate in the presence of a diluent, or (δ) are reacted with salicylic acid or esters thereof of the general formula (X)

(X)

in which

R represents hydrogen or alkyl, if appropriate in the presence of an acid acceptor and if appropriate in the presence of a diluent (cf. also EP-A 371240 and the preparation examples).

The aryl iso(thio)cyanates of the formula (VI) required as precursors are known and/or can be prepared by processes known per se (cf. DE-OS (German Published Specification) 2201668; DE-OS (German Published Specification) 703838; JP-A 60/097980—cited in Chem. Abstracts 03:141961; U.S. Pat. No. 5061310; Preparation Examples).

The aryl iso(thio)cyanates of the formula (VI) are obtained when arylamines of the general formula (XI)

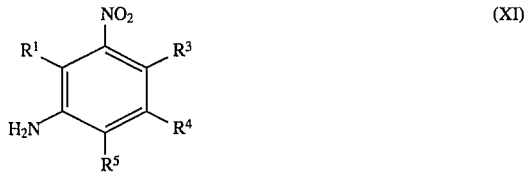

in which $R^1$, $R^3$, $R^4$ and $R^5$ have the abovementioned meanings, are reacted with phosgene or with thiophosgene, if appropriate in the presence of a diluent, such as, for example, toluene or chloroform and water, at temperatures between $-10°$ C. and $120°$ C.

The precursors of the formulae (VII), (VIII), (IX) and (X) are known and/or can be prepared by processes known per se (cf. EP-A 371240; J. Heterocycl. Chem. 27, 25 (1990), J. Chem. Soc., Perkin Trans 1, 1992, 2393; Chem. Pharm. Bull. 31, 1896 (1983)).

Process (a) according to the invention is carried out using a reducing agent and, if appropriate, a reaction auxiliary. All reducing agents conventionally used for reducing nitro compounds to amino compounds and, if appropriate, reaction auxiliaries to be used in this context may be employed.

The following reducing agents (and, if appropriate, reaction auxiliaries to be employed in this context) may be mentioned as being preferred:

metals, such as iron, cobalt, nickel, zinc or tin, in the presence of acids, such as, for example, acetic acid.

Hydrogen, in the presence of hydrogenation catalysts, such as Raney nickel, Raney cobalt, platinum or palladium, and also metal hydride complexes, such as lithium aluminium hydride, sodium borohydride or potassium borohydride, furthermore also sulphides, such as sodium sulphide or potassium sulphide, dithionites, such as sodium dithionite and potassium dithionite, formates, such as sodium formate and potassium formate.

Process (a) according to the invention for the preparation of the new aminoaryl-1,3-oxazine-2,4-diones of the formula (I) is preferably carried out using diluents. Diluents which are suitable are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, alcohols, such as methanol, ethanol and isopropanol, carboxylic acids, such as formic acid, acetic acid and propionic acid, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide, and also water.

When carrying out process (a) according to the invention, the reaction temperatures can be varied within a substantial range. In general, this process is carried out at temperatures between $0°$ C. and $150°$ C., preferably at temperatures between $10°$ C. and $100°$ C.

Process (a) according to the invention is generally carried out under atmospheric pressure or under elevated or reduced pressure (generally between 0.1 and 100 bar).

To carry out process (a) according to the invention, the starting substances required in each case are generally employed in approximately stoichiometric amounts. However, it is also possible to use one of the two components employed in each case in a larger excess. In general, the reactions are carried out in a suitable diluent in the presence of a reaction auxiliary, and the reaction mixture is stirred for several hours at the temperature required in each case. Working-up in process (a) according to the invention is carried out in each case by customary methods (cf. the preparation examples). Formula (Ia) provides a general definition of the amino-aryl-1,3-oxazine-2,4-diones to be used as starting substances in process (b) according to the invention for the preparation of compounds of the formula (I).

In formula (Ia), Q, $R^1$, $R^3$, $R^4$, $R^5$, $R^6$ and $R^7$ preferably, or in particular, have those meanings which have already been mentioned above in connection with the description of the compounds of the formula (I) according to the invention as being preferred, or particularly preferred, for Q, $R^1$, $R^3$, $R^4$, $R^5$, $R^6$ and $R^7$.

The starting substances of the formula (Ia) for process (b) according to the invention are new compounds according to the invention; they can be prepared by process (a) according to the invention.

Formula (III) or (IV) provides a general definition of the electrophilic compounds furthermore to be used as starting substances in process (b) according to the invention.

In these formulae, $R^2$ preferably, or in particular, has the meaning which has already been mentioned above in connection with the description of the compounds of the formula (I) according to the invention as being preferred, or particularly preferred, for $R^2$;

$A^1$ preferably represents $C_1$-$C_4$-alkyl, in particular methyl, ethyl or n- or i-propyl;

$X^1$ preferably represents chlorine, bromine, iodine or the group —O—$SO_2$—O—$A^1$, in particular chlorine, bromine, iodine, methoxysulphonyloxy and ethoxysulphonyloxy;

$X^2$ preferably represents fluorine, chlorine, bromine, acetoxycarbonyl or trifluoroacetoxycarbonyl, in particular chlorine or bromine.

The starting substances of the formulae (III) and (IV) are known chemicals for organic synthesis.

Formula (V) provides a general definition of the isocyanates to be used, if appropriate, as starting substances in process (b) according to the invention.

In formula (V), $R^8$ preferably represents $C_1$-$C_4$-alkyl, in particular methyl or ethyl.

The starting substances of the formula (V) are known chemicals for organic synthesis.

Process (b) according to the invention for the preparation of the new compounds of the formula (I) is preferably carried out using diluents. Diluents which are suitable are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

Acid acceptors which can be employed in process (b) according to the invention are all acid-binding agents which can customarily be used for reactions of this type. The following are preferably suitable: alkali metal hydrides and alkaline earth metal hydrides, such as lithium hydride, sodium hydride, potassium hydride and calcium hydride, alkali metal hydroxides and alkaline earth metalhydroxides, such as lithiumhydroxide, sodium hydroxide, potassium hydroxide and calcium hydroxide, alkali metal carbonates, alkali metal hydrogen carbonares, alkaline earth metal carbonates and alkaline earth metal hydrogen carbonates, such as sodium carbonate, potassium carbonate, sodium hydrogen carbonate or potassium hydrogen carbonate, and also calcium carbonate, alkali metal acetates, such as sodium acetate and potassium acetate, alkali metal alcoholares, such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium burylate, potassium isobutylate and potassium tert-burylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethyl-, 2-ethyl-, 4-ethyl- and 5-ethyl-2-methylpyridine, 1,5-diazabicyclo[4.3.0]non-5-ene (DBN), 1,8-diazabicyclo[5.4.0]undec-7-ene (DBU) and 1,4-diazabicyclo[2.2.2]-octane (DABCO).

When carrying out process (b) according to the invention, the reaction temperatures can be varied within a substantial range. In general, this process is carried out at temperatures between −20° C. and +100° C., preferably at temperatures between −10° C. and +80° C.

In general, process (b) according to the invention is carried out under atmospheric pressure. However, it is also possible to carry out this process under elevated or reduced pressure.

To carry out process (b) according to the invention, the starting substances required in each case are generally employed in approximately equimolar amounts. However, it is also possible to use one of the two components employed in each case in a larger excess. In general, the reactions are carried out in a suitable diluent, if appropriate in the presence of an acid acceptor, and the reaction mixture is stirred for several hours at the temperature required in each case. Working-up in process (b) according to the invention is carried out in each case by customary methods (of. the preparation examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera:
Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.
Dicotyledon cultures of the genera:
Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.
Monocotyledon weeds of the genera:
Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.
Monocotyledon cultures of the genera:
Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, lawns, turf and pasture-land, and for the selective combating of weeds in annual cultures.

The compounds of the formula (I) according to the invention are particularly suitable for selectively combating dicotyledon weeds in mono- and dicotyledon cultures, mainly by the post-emergence method.

To such an extent, the compounds of the formula (I) also show a fungicidal activity, for example against Pyricularia oryzae in rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamideand dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifopbutyl, haloxyfop-methyl and quizalofop-ethyl; azinones such as, for example, chloridazon and norflurazon; carbamates such as, for example, chlorpropham, desmedipham, phenmediphamand propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl, triasulfuron and tribehuron-methyl; thiocarhamares such as, for example, butylate, cycloate, diallate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The mount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

Preparation Examples

EXAMPLE 1

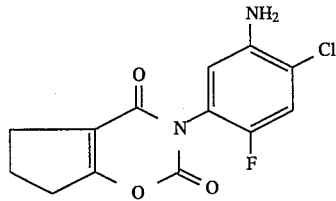

(Process (a))

5.6 g (0.1 mol) of iron powder are added in portions at room temperature (20° C.) to a mixture of 3.27 g (0.01 mol) of 3-(4-chloro-2-fluoro-5-nitrophenyl)-2,4,5,6,7-hexahydrocyclopent[e]-1,3-oxazine-2,4(3H,5H)-dione, 4.5 ml of acetic acid, 4.5 ml of water and 20 ml of ethyl acetate. Stirring is continued for 16 hours, 20 ml of ethyl acetate are added, and the mixture is filtered through silica gel with suction. After the filtrate has been washed using saturated sodium hydrogen carbonate solution and water, dried over sodium sulphate, filtered and concentrated, 2.70 g (91% of theory) of 3-(5-amino-4-chloro-2-fluorophenyl)-2,3,4,5,6,7-hexahydrocyclopenta[e]-1,3-oxazine-2,4-dione of melting point 93° C. are obtained.

$^1$H NMR (80 MHz, CDCl$_3$, δ): 7.19 (d, 1H, J=9.0 Hz); 6.64 (d, 1H, J=7.0 Hz) 4.00 (bs, 2H); 2.86 (dt, 2H, J=8.0 Hz, J=2 Hz); 2.76 (dr, 2H, J=8.0 Hz, J=2 Hz); 2.17 (quintet, 2H, J=8.0 Hz).

EXAMPLE 2

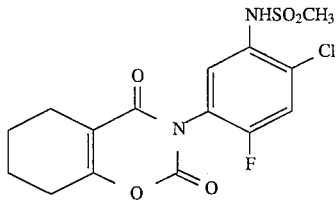

(Process (b))

0.09 g (0.0011 mol) of pyridine and 0.13 g (0.0011 mol) of methanesulphonyl chloride are added at 0° C. to a solution of 0.3 g (0.001 mol) of 3-(5-amino-4-chloro-2-fluorophenyl)-2,3,4,5,6,7,8-heptahydrocyclohexa[e]-1,3-oxazine-2,4-dione, and stirring is continued overnight. After working-up analogously to Example 1, 0.34 g (88% of theory) of 3-(5-methylsulphonyl-4-chloro-2-fluorophenyl)-2,3,4,5,6,7,8-heptahydrocyclohexa[e]-1,3-oxazine-2,4-dione is obtained as an oil.

$^1$H NMR (80 MHz, CDCl$_3$, δ): 7.58 (d, 1H, J=8.0 Hz); 7.29 (d, 1H, J=9.0 Hz); 6.94 (bs, 1H); 2.97 i (s, 3H); 2.45 (m, 2H); 2.35 (m, 4H); 1.82 (m, 2H); 1.69 (m, 2H).

0.71 g (0.009 mol) of pyridine and then 1.13 g (0.009 mol) of ethanesulphonyl chloride are added, at 0° C., to a solution of 2.37 g (0.008 mol) of 3-(5-amino-4-chloro-2-fluorophenyl-2,3,4,5,6,7-hexahydrocyclopenta[e]-1,3-oxazine-2, 4(3H,5H)-dione in 11 ml of methylene chloride. After the reaction mixture has been stirred overnight at room temperature (20° C.), it is poured into 10 ml of water, and the phases are separated. The aqueous phase is extracted using methylene chloride, and the combined methylene chloride extracts are washed using sodium hydrogen carbonate solution and water.

Drying over sodium sulphate and concentration gives 2.73 g (88% of theory) of 3-(5-ethylsulphonylamino-4-chloro-2-fluorophenyl)-2,3,4,5,6,7-hexahydrocyclopentae[e]-1,3-oxazine-2,4(3H,5H)-dione of melting point 166° C.
$^1$H NMR (80 MHz, CDCl$_3$, δ): 7.69 (d, 1H, J=8.0 Hz); 7.35 (d, 1H, J=9.0 Hz); 6.87 (s, 1H); 3.13 (q, 2H, J=8.0 Hz); 2.88 (t, 2H, J=8.0 Hz); 2.76 (t, 2H, J=8.0 Hz); 2.19 (quintet, 2H, J=8.0 Hz); 1.36 (t, 3H, J=8.0 Hz).

The compounds of the formula (I) which are listed in Table 3 below can be prepared analogously to Examples 1 to 3 and following the general description of the preparation processes according to the invention.

TABLE 3

Preparation Examples of the compounds of the formula (I)

(I)

| Ex. No. | R$^1$ | -N(A)(R$^2$) | R$^3$ | R$^4$ | R$^5$ | R$^6$ | R$^7$ | Q | Phys. Data |
|---|---|---|---|---|---|---|---|---|---|
| 4 | H | NHSO$_2$CH$_3$ | Cl | H | F | —(CH$_2$)$_3$— | | O | m.p. 82° C. |
| 5 | H | NHSO$_2$CHC$_6$H$_5$ | Cl | H | F | —(CH$_2$)$_3$— | | O | Oil a) |
| 6 | H | NH$_2$ | Cl | H | F | —(CH$_2$)$_4$— | | O | Oil b) |
| 7 | H | NH$_2$ | Cl | H | F | CH$_3$ | C$_2$H$_5$ | O | Oil c) | a) $^1$H NMR (80 MHz, CDCl$_3$, δ): 7.26(m, 5H), 7.15(d, 1H, J=9.0 Hz); 6.41(d, 1H, J=8.0 Hz); 4.49(bs, 1H), 4.23(d, 2H, J=5 Hz); 2.75(t, 2H, J=9.0 Hz); 2.66(t, 2H, J=9.0 Hz); 2.07(quintet, 2H, J=8.01)
b) $^1$H NMR (80 MHz, CDCl$_3$, δ): 7.19(d, 1H, J=9.0 Hz); 6.65(d, 1H, J=8.0 Hz); 4.00(bs, 2H); 2.51(m, 2H); 2.42(m, 2H); 1.87(m, 2H); 1.76(m, 2H)
c) $^1$H NMR (80 MHz, CDCl$_3$, δ): 7.18(d, 1H, J=9.0 Hz); 6.65(d, 1H, J=8.0 Hz); 4.00(bs, 2H); 2.41(g, 2H, J=8.0 Hz); 2.27(s, 3H); 1.11(t, 3H, J=8.0 Hz).

Starting substances of the formula (II)

EXAMPLE 3

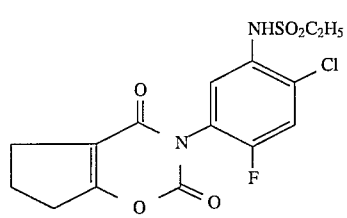

(Process (b))

EXAMPLE (II-1)

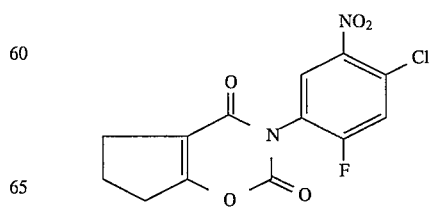

12.6 g (0.075 mol) of 2,2-dimethyl-4,5,6,7-tetrahydropenta-1,3-dioxin-4-one are added dropwise at 140° C. to a solution of 13.5 g (0.0625 mol) of 4-chloro-2-fluoro-5-nitrophenyl isocyanate in 50 ml of 1,2-dichlorobenzene; stirring of the reaction mixture is then continued for 2 hours at 140° C. After the mixture has been concentrated in vacuo, the residue is purified by column chromatography on silica gel.

13.4 g (66% of theory) of 3-(4-chloro-2-fluoro-5-nitrophenyl)-2,3,4,5,6,7-hexahydropenta[e]-1,3-oxazine-2,4-dione of melting point 168° C. are obtained.

$^1$H NMR (80 MHz, CDCl$_3$, δ): 9.03 (d, 1H, J=8.0 Hz); 7.48 (d, 1H, J=9.0 Hz); 2.89 (m, 2H); 2.78 (m, 2H); 2.20 (quintet, 2H, J=8.0 Hz).

EXAMPLE (II-2)

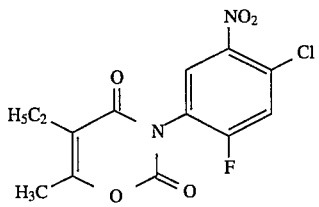

5.10 g (0.03 mol) of 5-ethyl-2,2,6-trimethyl-4H-1,3-dioxin-4-one are slowly added dropwise to a solution of 5.41 g (0.025 mol) of 4-chloro-2-fluoro-5-nitro-phenyl isocyanate in 20 ml of o-dichlorobenzene, and the mixture is subsequently heated for 2 hours at this temperature. After the volatile components have been removed, 3.70 g (45% of theory) of 3,4-dihydro-3-(4-chloro-2-fluoro-5-nitrophenyl)-5-ethyl-6-methyl-2H-1,3-dione are isolated as an oil by column chromatography over silica gel.

$^1$H NMR (80 MHz, CDCl$_3$, δ): 8.04 (d, 1H, J=8.0 Hz); 7.48 (d, 1H, J=9.0 Hz); 2.43 (q, 2H, J=8.0 Hz); 2.31 (s, 3H); 1.12 (t, 3H, J=8.0 Hz).

Starting substances of the formula (VI)

EXAMPLE (VI-1)

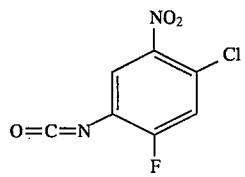

Dry HCl gas is passed into a solution of 66.7 g (0.35 mol) of 4-chloro-2-fluoro-5-nitroaniline in 1180 ml of toluene at 0° to 5° C. until the solution is saturated. 34.7 g (0.35 ml) of phosgene are subsequently metered in, and the mixture is heated slowly at 85° C. After a further 17.3 g (0.175 mol) of phosgene have been added and the mixture has been heated at 85° C. (1 h), the batch is flushed with nitrogen until free from phosgene and cooled. Removal of the precipitate by filtration and concentration gives 28.6 g (37.7% of theory) of 4-chloro-2-fluoro-5-nitrophenyl isocyanate of melting point 43°–46° C.; boiling point 125° C. at 0.3 torr (bulb-tube distillation).

$^1$H NMR (80 MHz, CDCl$_3$, δ): 7.74 (d, 1H, J=8.0 Hz); 7.40 (d, 1H, J=9.0 Hz). IR (film, V): 2255, 1546, 1348 (cm$^{-1}$).

The compounds of the formula (VI) listed in Table 4 below can be prepared analogously.

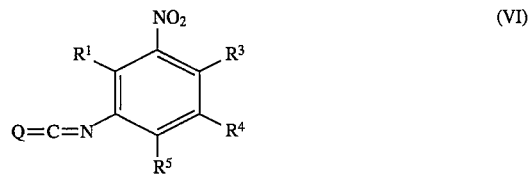

TABLE 4

| Examples of the compounds of formula (VI) | | | | |
|---|---|---|---|---|
| R$^1$ | R$^3$ | R$^4$ | R$^5$ | Q |
| H | Cl | H | H | O |
| H | Cl | H | F | O |
| H | Cl | H | Cl | O |
| H | Br | H | H | O |
| H | Br | H | F | O |
| H | Br | H | Cl | O |
| H | CN | H | H | O |
| H | CN | H | F | O |
| H | CN | H | Cl | O |
| H | CH$_3$ | H | F | O |
| H | Cl | H | F | S |
| H | CN | H | H | S |
| H | CN | H | F | S |

Use Example:

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

The figures denote:

0%=no action (like untreated control)

100%=total destruction

In this test, a powerful action against weeds such as Abutilon, Datura, Ipomoea, Portulaca, Solanum and Xanthium, where the damage is in each case between 90 and 100%, combined with a good tolerance by crop plants, such as, for example, wheat, is shown in this test, for example, by the compounds of Preparation Examples 1, 3 and 4.

It will be understood that the specification and examples are illustrative but not limitative of the present invention and that other embodiments within the spirit and scope of the invention will suggest themselves to those skilled in the art.

What is claimed is:

1. An aminoaryl-1,3-oxazine-2,4-dione of the formula

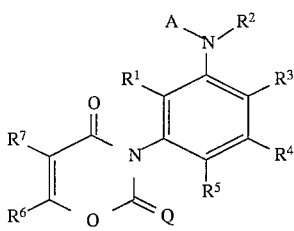 (I)

in which

A represents hydrogen or $C_1$–$C_6$-alkyl,

Q represents oxygen or sulphur, $R^1$ represents hydrogen or halogen, $R^2$ represents, $C_2$–$C_6$-alkenyl, $C_2$–$C_6$-alkynyl, $C_1$–$C_6$-alkylcarbonyl, $C_1$–$C_6$-alkoxycarbonyl, $C_1$–$C_6$-alkylaminocarbonyl, $C_1$–$C_6$-alkylsulphonyl, or di($C_1$–$C_4$-alkyl)-aminosulphonyl wherein each of said groups is optionally substituted by halogen or $C_1$–$C_4$-alkoxy, $R^2$ furthermore represents phenyl, phenylcarbonyl, phenyl-$C_1$–$C_4$-alkyl, phenylsulphonyl or phenyl-$C_1$–$C_4$-alkylsulphonyl wherein each said groups is optionally substituted by halogen, cyano, nitro, carboxyl, carbamoyl, optionally substituted $C_1$–$C_4$-alkyl, optionally substituted $C_1$–$C_4$-alkoxy, optionally substituted $C_1$–$C_4$-alkylthio, optionally substituted $C_1$–$C_4$-alkylsulphinyl, optionally substituted $C_1$–$C_4$-alkylsulphonyl or $C_1$–$C_4$-alkoxycarbonyl wherein the optionally substituent is halogen, $R^3$ represents hydrogen, halogen, cyano, methyl, trifluoromethyl or methoxycarbonyl, $R^4$ represents hydrogen or halogen, $R^5$ represents hydrogen or halogen, $R^6$ represents hydrogen, halogen, or represents $C_1$–$C_4$-alkyl or phenyl, each of which is optionally substituted by halogen, and $R^7$ represents hydrogen, halogen, or represents $C_1$–$C_4$-alkyl or phenyl, each of which is optionally substituted by halogen, or together with $R^6$ represents $C_3$–$C_5$-alkanediyl, or together with $R^6$ forms a benzo group.

2. A compound according to claim 1 which has the formula

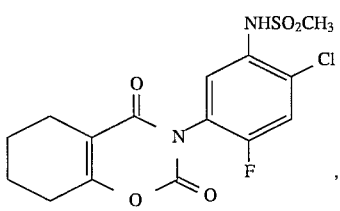

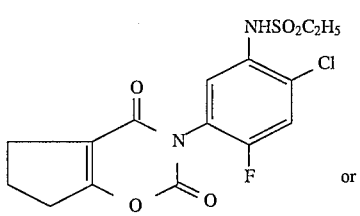 or

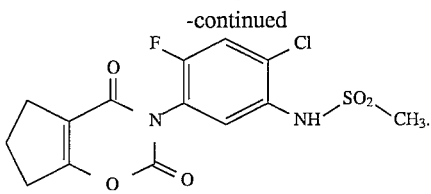

3. An aminoaryl-1,3-oxazine-2,4-dione according to claim 1, wherein

A represents hydrogen or $C_1$–$C_4$-alkyl,

Q represents oxygen or sulphur, $R^1$ represents hydrogen, fluorine, chlorine or bromine, $R^2$ represents a radical selected from the group consisting of $C_2$–$C_4$-alkenyl, $C_2$–$C_4$-alkynyl, $C_1$–$C_4$-alkylcarbonyl, $C_1$–$C_4$-alkoxycarbonyl, $C_1$–$C_4$-alkylaminocarbonyl or $C_1$–$C_4$-alkylsulphonyl or di($C_1$–$C_3$-alkyl)aminosulphonyl, each of which is optionally substituted by fluorine, chlorine, methoxy or ethoxy, $R^2$ furthermore represents a radical selected from the group consisting of phenyl, phenylcarbonyl, phenyl-$C_1$–$C_3$-alkyl, phenylsulphonyl or phenyl-$C_1$–$C_3$-alkylsulphonyl, each of which is optionally substituted by halogen, cyano, nitro, carboxyl, carbamoyl, optionally substituted $C_1$–$C_3$-alkylsulphonyl or $C_1$–$C_3$-alkoxycarbonyl wherein the optional substituent is fluorine or chlorine, $R^3$ represents hydrogen, fluorine, chlorine, bromine, cyano, methyl, trifluoromethyl or methoxycarbonyl, $R^4$ represents hydrogen, fluorine, chlorine or bromine, $R^5$ represents hydrogen, fluorine, chlorine or bromine, $R^6$ represents hydrogen, fluorine, chlorine, bromine, or represents $C_1$–$C_3$-alkyl or phenyl, each of which is optionally substituted by fluorine and/or chlorine, or together with $R^6$ represents $C_3$–$C_4$-alkanediyl, or together with $R^6$ forms a benzo group.

4. A nitroaryl-1,3-oxazine-2,4-dione of the general formula (II)

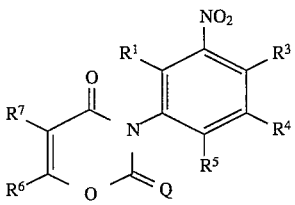 (II)

wherein

Q represents oxygen or sulphur, $R^1$ represents hydrogen or halogen, $R^3$ represents hydrogen, halogen, cyano, methyl, trifluoromethyl or methoxycarbonyl, $R^4$ represents hydrogen or halogen, $R^5$ represents hydrogen or halogen, $R^6$ represents phenyl which is optionally substituted by halogen, and $R^7$ represents phenyl which is optionally substituted by halogen, or together with $R^6$ represents $C_3$–$C_5$-alkanediyl, or together with $R^6$ forms a benzo group.

5. An amino-1,3-oxazine-2,4-dione of the general formula (Ia)

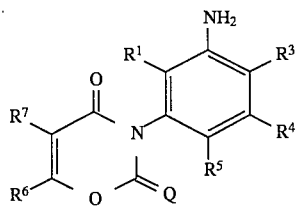

(Ia)

wherein
Q represents oxygen or sulphur,
R¹ represents hydrogen or halogen,
R³ represents hydrogen, halogen, cyano, methyl, trifluoromethyl or methoxycarbonyl,
R⁴ represents hydrogen or halogen,
R⁵ represents hydrogen or halogen,
R⁶ represents hydrogen, halogen, or represents $C_1$–$C_4$-alkyl or phenyl, each of which is optionally substituted by halogen, and
R⁷ represents hydrogen, halogen, or represents $C_1$–$C_4$-alkyl or phenyl, each of which is optionally substituted by halogen, or together with R⁶ represents $C_3$–$C_5$-alkanediyl, or together with R⁶ forms a benzo group.

6. A compound wherein such compound is 3-(5-amino-4-chloro-2-fluorophenyl)-2,3,4,5,6,7-hexahydrocyclopenta[e]-1,3-oxazin-2,4(3H, 5H)-dione of the formula

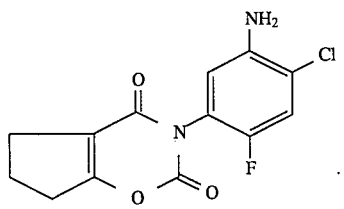

7. A compound according to claim 1 wherein such compound is 3-(5-ethylsulfonylamino-4-chloro-2-fluorophenyl)-2,3,4,5,6,7-hexahydrocyclopenta[e]-1,3-oxazin-2,4(3H,5H)-dione of the formula

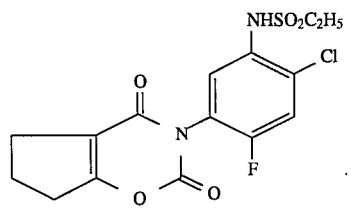

8. A compound according to claim 1 wherein such compound is 3-(5-methylsulfonylamino-4-chloro-2-fluorophenyl)-2,3,4,5,6,7-hexahydrocyclopenta[e]-1,3-oxazin-2,4(3H, 5H)-dione of the formula

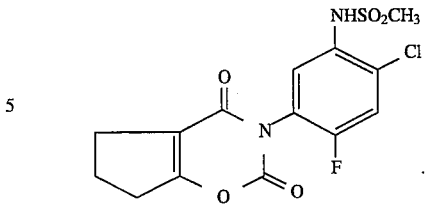

9. A herbicidal composition comprising a herbicidally effective amount of a compound according to claim 1 and a diluent.

10. A method of combating unwanted vegetation which comprises applying to such vegetation or to a locus from which it is desired to exclude such vegetation a herbicidally effective amount of a compound according to claim 1.

11. The method according to claim 10, wherein such compound is 3-(5-amino-4-chloro-2-fluorophenyl)-2,3,4,5,6,7-hexahydrocyclopenta[e]-1,3-oxazin-2,4(3H, 5H)-dione, 3-(5-ethylsulfonylamino-4-chloro-2-fluorophenyl)-2,3,4,5,6,7-hexahydrocyclopenta[e]-1,3-oxazin-2,4(3H, 5H)-dione or 3-(5-methylsulfonylamino-4-chloro-2-fluorophenyl)-2,3,4,5,6,7-hexahydrocyclopenta[e]-1,3-oxazin-2,4(3H, 5H)-dione.

12. An aminoaryl-1,3-oxazine-2,4-dione according to claim 1, wherein

A represents hydrogen, methyl or ethyl or i-propyl,
Q represents oxygen or sulphur,
R¹ represents hydrogen,
R² represents allyl, propargyl, or represents acetyl or propionyl, each of which is optionally substituted by fluorine or chlorine, or represents methoxycarbonyl, ethoxycarbonyl, methylaminocarbonyl or ethylaminocarbonyl, or represents methylsulphonyl or ethylsulphonyl, each of which is optionally substituted by fluorine or chlorine, or represents dimethylaminosulphonyl, or represents phenyl, benzoyl, benzyl, phenylsulphonyl or phenylmethylsulphonyl, each of which is optionally substituted by fluorine, chlorine, cyano, nitro, carboxyl, methyl, trifluoromethyl, methoxy or methoxycarbonyl,
R³ represents chlorine, bromine or cyano,
R⁴ represents hydrogen,
R⁵ represents hydrogen, chlorine or fluorine,
R⁶ represents hydrogen, chlorine, bromine, methyl or trifluoromethyl and
R⁷ represents hydrogen, chlorine, bromine, methyl or trifluoromethyl, or together with R⁶ represents trimethylene or tetramethylene.

* * * * *